United States Patent [19]

Brownlee et al.

[11] 4,014,346
[45] Mar. 29, 1977

[54] HERMETICALLY SEALED CARDIAC PACER SYSTEM AND RECHARGING SYSTEM THEREFOR

[75] Inventors: Robert R. Brownlee, State College; G. Frank O. Tyers, Hershey; Carl Volz, Sr., State College, all of Pa.

[73] Assignee: Research Corporation, New York, N.Y.

[22] Filed: June 26, 1975

[21] Appl. No.: 590,413

[52] U.S. Cl. .......................... 128/419 PS; 429/49
[51] Int. Cl.² .................................... A61N 1/36
[58] Field of Search ... 128/419 P, 419 PG, 419 PS, 128/419 R, 421, 422; 136/179, 167

[56] References Cited

UNITED STATES PATENTS

| | | | |
|---|---|---|---|
| 1,016,874 | 2/1912 | Edison | 136/179 |
| 3,683,932 | 8/1972 | Cole | 128/419 P |
| 3,835,864 | 9/1974 | Rasor et al. | 128/419 PS |
| 3,866,616 | 2/1975 | Purdy et al. | 128/419 PS |
| 3,888,260 | 6/1975 | Fischell | 128/419 PS |
| 3,893,870 | 7/1975 | Kozawa | 136/179 |

OTHER PUBLICATIONS

Evalenko et al. "Medical Instrumentation", Mar.-Apr., 1967, pp. 13–16.

*Primary Examiner*—William E. Kamm
*Attorney, Agent, or Firm*—Cooper, Dunham, Clark, Griffin & Moran

[57] ABSTRACT

An hermetically-sealed cardiac pacemaker which may be operated on a single non-rechargeable cell or a magnetic-induction-rechargeable mercury cell that is hermetically sealed along with an outgas alleviating material in a separate container within an integral stainless steel outer case, which case also houses the system electronics. The integral case is formed with an opening in which a closure plate is disposed in a recessed position and sealed about its periphery to the interior of the opening to form a receptacle in the exterior of the casing. The receptacle is filled with a biocompatible material to isolate the seal from the exterior of the casing and the case acts along with the internal electronics during recharging as a charging current regulator system which maintains a substantially constant power transfer from the charging transmitter to the internal receiver despite variations in their proximate spacing.

27 Claims, 10 Drawing Figures

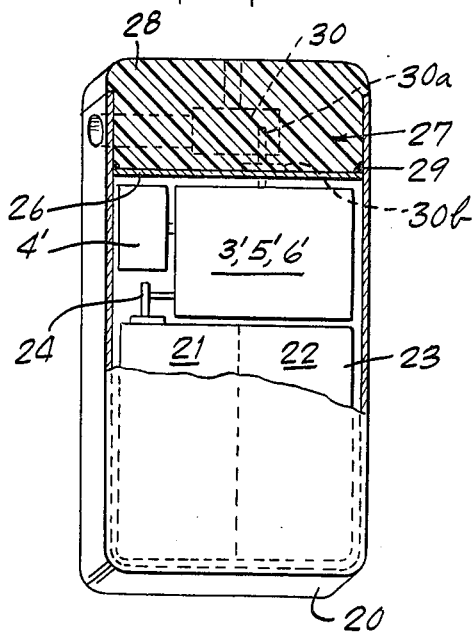
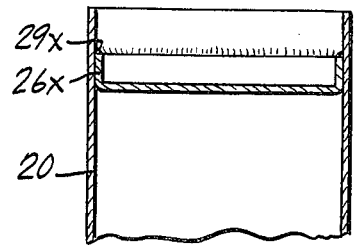
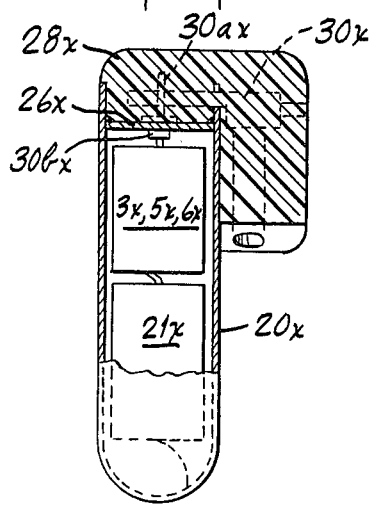
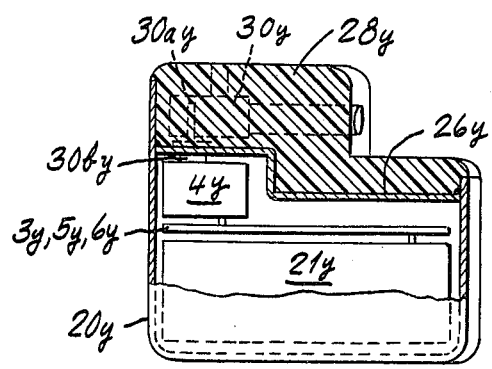
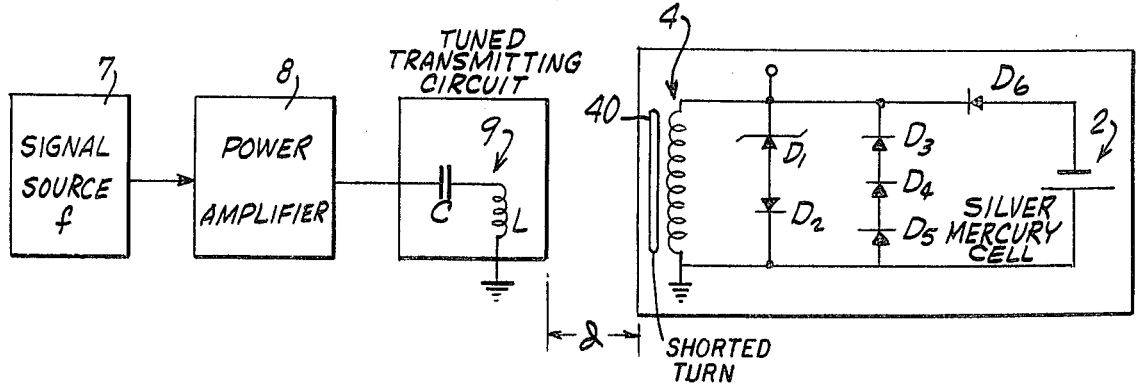

HERMETICALLY SEALED CARDIAC PACER SYSTEM AND RECHARGING SYSTEM THEREFOR

BACKGROUND

The present invention relates to cardiac pacers and particularly involves an hermetically-sealed pacer containing a single rechargeable cell.

Present commercially available non-rechargeable mercury-zinc battery powered inplantable cardiac pacemakers have a mean life of approximately 24 months and eventually fail from battery exhaustion or electronic component malfunction usually due to gradual absorption of body fluids through the pacemaker housing. More recently developed longer life units such as rechargeable and nuclear cell models have not as yet been fully proven by long clinical experience and even if functionally successful, could prove to be relatively expensive.

As a result there is a need for a safe, relatively inexpensive pacemaker which is hermetically sealed against moisture intrusion and which is capable of an extended long life. Such a device should also be light in weight, have a shape and surface condition compatible with its biological environment, be immune to radio frequency fields and have components which are readily available and of proven reliability. The present invention is intended to fulfill all of these requirements.

SUMMARY

The present invention embodies an hermetically-sealed cardiac pacemaker which may be operated on a single, magnetic-induction-rechargeable mercury-silver cell that is sealed along with an outgas alleviating means in a separate container within a suitable metallic outer case, which case also houses the system electronics. Both the container and the case are hermetically sealed in an improved manner and the case acts along with the internal electronics as a charging current regulator system which maintains a substantially constant power transfer from the charging transmitter to the internal receiver within clinically applicable variations in their proximate spacing.

BRIEF DESCRIPTION OF THE DRAWINGS

FIG. 2 is a perspective view of a preferred embodiment of an implantable pacemaker unit in accordance with the present invention. FIG. 2a illustrates an alternate form of end cap for use with the pacemaker unit of FIG. 2.

FIG. 3 is an alternate form of implantable pacemaker unit having a different configuration from that of FIG. 2.

FIG. 4 is a further alternate form of implantable pacemaker unit illustrating another suitable configuration in accordance with the present invention.

FIG. 5 illustrates a preferred embodiment of recharging circuitry for use in a cardiac pacer system in accordance with the present invention.

DETAILED DESCRIPTION

Figure 1:
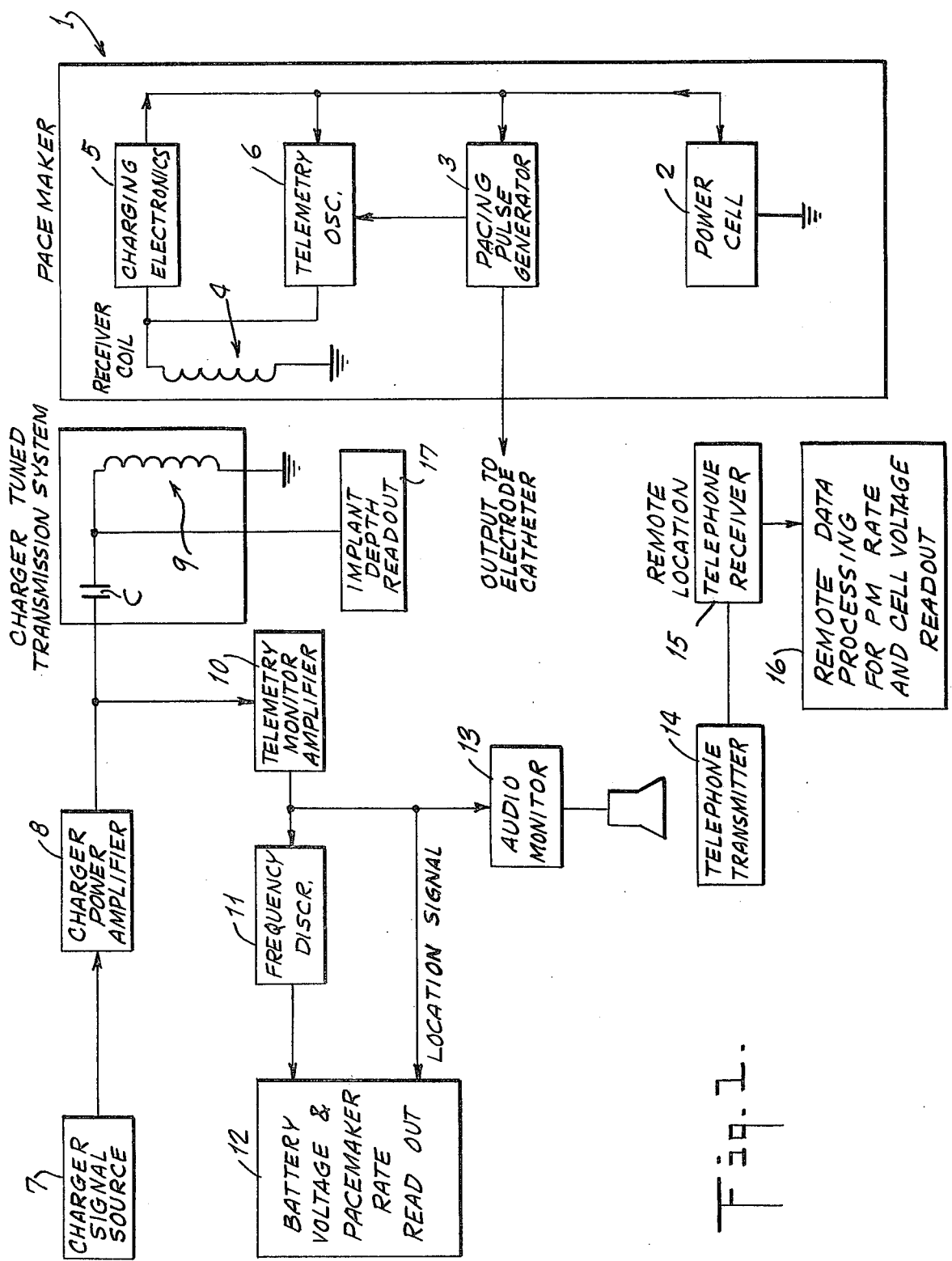
FIG. 1 is a functional block diagram illustrating a cardiac pacemaker system comprising external charging and monitoring apparatus and an implanted pacemaker unit in accordance with the present invention.

A functional block diagram illustrating a cardiac pacemaker system in accordance with the present invention is shown in FIG. 1.

The implanted pacemaker unit 1 comprises a single rechargeable cell 2 which powers a suitable pacing pulse generator 3 for supplying an output via a signal catheter to a ventricular heart electrode, and a receiver coil 4 with charging electronics 5 for recharging the cell along with a telemetry oscillator 6 that provides remote readout of the cell voltage and pacing pulse rate. A preferred pacing pulse generator and telemetry oscillator are disclosed in our respective co-pending applications Ser. Nos. 590,409 and 590,414, filed concurrently herewith.

The external charging and monitoring unit comprises a charger signal source 7 and power amplifier 8, which provide an electromagnetic signal to a tuned circuit including condenser C and charger or transmitting coil 9. During the charging operation the charger coil 9 transmits electromagnetic energy, through the intact skin of the person in whom the pacemaker has been implanted, to the receiver coil 4. The charger coil 9 also may be used as a receiving coil during precharge and postcharge monitoring of the cell voltage and pacing pulse rate by sensing the signal from the telemetry oscillator 6 which is fed through the receiver coil 4. The received telemetry signal from the pacemaker is processed through a telemetry monitor amplifier 10 and may be converted by a frequency discriminator 11 into a reading on an appropriate meter 12, as well as being fed to an audio monitor 13 which converts it to an audio signals. The audio signal is also compatible in frequency to telephone transmission so that the telemetry data may be transmitted through a telephone transmitter 14 to a telephone receiver 15 and read out at a remote data center 16. An implant depth meter 17 may also be connected to the tuned circuit.

The pacemaker power cell 2 is preferably a rechargeable version of the primary silver modified zinc-mercury battery presently used in over 95 precent of all pacemakers. This rechargeable version, which is obtainable commercially, for example, as Mallory Model RMCC-1420S, based on present testing is estimated to be capable of a total functional life with- recharging of approximately twenty years. However, such electrochemical cells suffer from the problem of outgassing, that is, hydrogen gases are exuded from the cell continuously at low rates. This is a particular problem if it is desired to hermetically seal the case, as in the present invention, since outgassing will result in a pressure buildup inside the container and may attack the electronic components also housed therein. For the particular cell mentioned above, outgassing rates as high as 20 cc per year have been reported along with average rates of 6 to 7 cc per year. In the past, non-hermetic metal coverings over epoxy encased units, such as disclosed in U.S. Pat. No. 3,690,325, have been tried to permit outgassing while preventing the intrusion of body fluids, but have led to serious complications.

To overcome the outgassing problem, the present invention utilizes a hydrogen "getter" in the form, for example, of palladium sponge or lanthanum pentanickel. Measurements of the hydrogen absorption capabilities of palladium indicate that 85 cc of hydrogen can be collected for each gram of sponge used so that three grams of palladium sponge will provide a "getter life" in excess of 10 years when used with a single cell as contemplated by the present invention. Further, lanthanum pentanickel would appear to offer even better results as the getter material.

More particularly, a preferred embodiment of implantable pacemaker unit 1 in accordance with the present invention is shown in greater detail in FIG. 2. It will be seen that in order to prevent attack of the gas on the electronic components, the electrochemical cell 21 and the getter material 22 are disposed in a separate hermetically sealed container 23 within the main outer casing 20 of the pacemaker, and appropriate terminals or leads 24 extending through the container 23 are connected to the remainder of the electronics 3', 5', and 6', which in turn are connected to receiver coil 4'. The hermetic sealing of this interior container 23 may be accomplished by any known technique consistent with avoiding damage to the contents as it is protected within the sealed outer casing 20.

However, particular problems are encountered in providing an hermetic seal for the entire implantable pacemaker. Such sealing while using a sealing process that does not generate excess heat so as to prevent damage to the electronic components must also be accomplished using a method for final sealing of the unit that is body-compatible. In the past, the use of metallic outer casings usually required welded seams to be of the same metal as the case to avoid "local action" and adverse chemical reactions with body fluids. The present invention overcomes this and other problems by employing an integral metallic outer case, such as of deep drawn stainless steel in a rectangular configuration (FIG. 2), having an end opening to permit the insertion of the components. A lid or cover member in the form of a plate 26 is disposed within the opening in a recessed manner and its periphery is finally sealed to the inner walls of the opening by soldering with suitable low temperature solder. As particularly seen in FIG. 2, this lid configuration forms a recessed end or receptable 27 in the case 20 which is then covered with body-acceptable epoxy or other suitable biocompatible sealing material which forms a sealing member 28. The final epoxy sealing member over the solder seam 29 protects the seam from body fluids and also forms the enclosure for the pacemaker signal catheter receptacle 30.

As a result of this arrangement and sealing technique, the need for high temperature welds is obviated and the casing seam is of minimum length and isolated from direct contact with body tissue or fluids. Alternate forms of case configuration are shown in FIGS. 3 and 4 where like numerals with respective distinguishing letter suffixes are used to identify components corresponding to those shown in FIG. 2. It will be seen that although casing 20x in FIG. 3 is cylindrical in form and cover member 26y in FIG. 4 is not a flat plate, all the configurations allow the final hermetic seal to be isolated with a biocompatible interface protective material. The interface barrier allows the use of low temperature solders and nonidentical case and weld materials. Use of an epoxy or other non-metallic biocompatible material such as segmented polyurethane for the sealing member 28 over the soldered or welded seam 29 not only prevents any serious attack of body fluids on the seam but also prevents any attack of the seam material on human tissue adjacent to the implant. Low melting temperature (430° F) tin-silver solders are commercially available that are considered to be relatively nontoxic, and although they would be unacceptable for exposed joints in long-term implants due to chemical reaction, with the epoxy cover protection they can make suitable soldered seams for the present invention.

Also as a result of the present sealing technique, the receptacle 30, which is used for entrance or exit of biologic or device generated signals from the pacemaker interior, is mechanically secured and protected by the epoxy member 28. The member 28 also acts to house and insulate the point of connection of the signal catheter and cardiac electrode for the pacemaker function to the receptacle 30. The receptacle leads 30a passing through the plate 26 to the receptacle 30 are sealed via a glass-to-metal seal electrical feedthrough 30b.

A preferred method of assembling pacemakers of the forms such as shown in FIGS. 2 through 4 will now be described in greater detail. The first step is the provision of an extruded metallic can that is seamless, except for a single open end. The can may be of a suitable metal, such as stainless steel or titanium, and of any suitable form for containing the electronics including the three configurations shown. After the proper insertion of the electronics, the can is sealed by the insertion of a lid or cap member, which may be in the form of a plate, in the open end in a recessed position so that a "well" is formed in the case for use as a receptacle for the biocompatible non-metallic barrier.

The plate is preferably sealed to the can interior by known low temperature techniques, such as soldering or electron beam welding, to avoid heating of the internal components. If the can and cap member are selected to be of stainless steel, the interior of the can where the plate is located, the edge of the plate, and the feedthrough area should be pretinned with a caustic flux such as Welco 500 or the equivalent, to achieve "wetting" and adherance to the casing, which preferably is stainless steel of the type 316L suitable for implant use. Tin-silver solders such as Welco No. 5 or the equivalent may be used to form the seam. After tinning, thorough cleaning of all parts with industrial solvents is recommended to ensure removal of the highly corrosive and conductive flux residues. Sonic cleaning in an acetone bath follows by a second sonic cleaning with isoproponol has also been used with success in flux removal.

For final assembly and joining of the plate to the inside of the main case, after installation and potting of the electronics and energy source, non-corrosive fluxes that form non-tacky and nonconductive residues should be employed. Ersin liquid flux type 4370 or equivalent is a satisfactory final assembly flux. Cleaning of the well area of flux residues after the joint is soldered using tin-silver solders, such as Welco No. 5 or equivalent, is then accomplished by swabbing with acetone and isoproponol. At this stage, sonic cleaning is not recommended since the electronics and battery would be subjected to the acoustic energy. The well area after cleaning is then sand-blasted to improve adherance of the epoxy or other barrier to the steel. Various chemical treatments, such as chemical etching, to improve adherance may also be found suitable. Molding fixtures for forming the output receptacle and catheter entrance cavities should be coated with a release agent such as Miller Stevenson MS-122 or the equivalent, prior to pouring the epoxy barrier. Care should be exercised to prevent release materials from contaminating the well area.

The final barrier is formed with a biocompatible epoxy such as Hysol R-2038 resin and H2-3404 hardener or equivalents, so that the only materials in contact with tissue at the implant site are the stainless steel case, the epoxy barrier and the insulation used on the signal catheter which is typically a silicone rubber.

An alternate form of cover member 26 is shown in FIG. 2a wherein the cover plate is formed with an upstanding peripheral lip 26x around whose uppermost edge a sealing weld 29x is formed. This configuration is particularly suitable for use with welds, such as would probably be required with a titanium case, since the lip extends the lip extends the length of the thermal path from the weld joint to the internal electronics package to minimize thermal transmission thereto.

Figure 7:
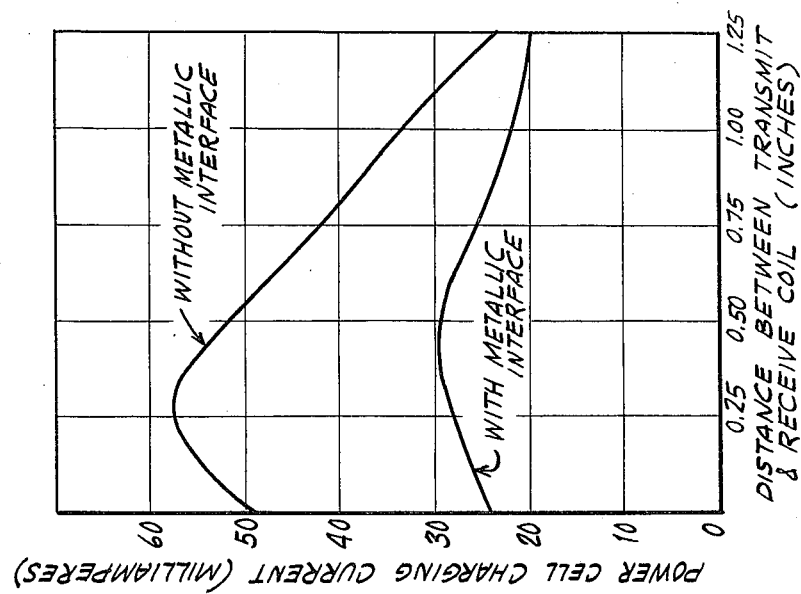
FIG. 7 is a plot showing a comparison of power cell charging current regulation with and without the shorted turn regulator formed by the metallic interface in the circuitry of FIG. 5.
Figure 6:
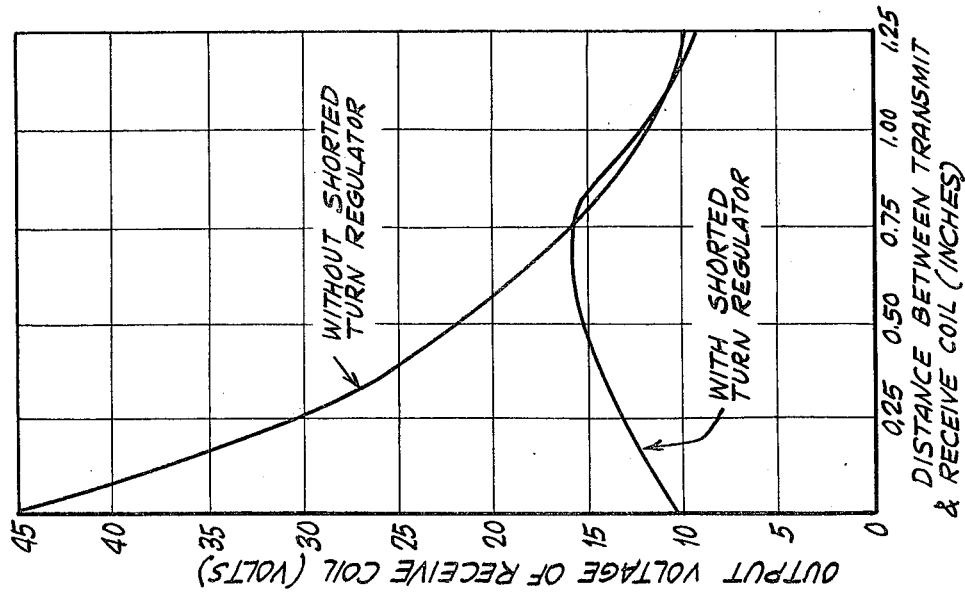
FIG. 6 is a plot showing a comparison of electromagnetic energy transfer with and without the shorted turn regulator in the circuitry of FIG. 5.

While the metallic case is extremely suitable for accomplishing hermetic sealing in the manner described when a non-rechargeable power cell, such as a lithium cell, is used, it could pose a problem with regard to the transfer of the electromagnetic energy from the external charger coil 9 to the internal receiver coil 4, when a rechargeable cell is used, since the metallic interface can cause losses with attendant heating problems during the charging process as a consequence of induced eddy currents. However, in accordance with the present invention this heat energy loss is turned to advantage through a special tuned transmitting system that not only aids in regulating the cell charging current, but also acts to regulate the transmitted power so that case heating is minimized as implant depth is reduced. The system, shown schematically in FIG. 5, utilizes a closed link or shorted turn 40 which may be provided by the wall of the metallic case. The receiver coil 4 is placed in proximity to the shorted turn 40 and the transmitting circuit (LC) is tuned to resonance at a frequency which is chosen so that losses in the metallic case are reflected to the transmitting circuit and thereby regulate the input power as a function of the spacing d between the transmitting and receiver coils. The regulating function of the shorted turn 40 at the receiver coil 4 is accomplished by reflecting a variable loss with variable spacing to the transmitting coil 9 to thereby modify the transmitting circuit Q with distance. As the distance d between the transmitter and shorted turn is reduced, the Q is reduced, raising the transmitting circuit (LC) impedance and thereby reducing the power input to the transmitting coil 9. The net effect is a more constant transfer of power into the receiver coil 4 as $d$ is varied. The advantage of the shorted turn 40 is illustrated in FIG. 6 which contains a plot of the output voltage of the receiver coil with and without the shorted turn 40 as the distance $d$ between the two coils is varied. It will be seen that the variation in the output voltage is considerably reduced with the shorted turn in place. FIG. 7 is a plot of battery charging current as a function of variable spacing with and without the metallic (stainless steel) interface as the shorted turn and further illustrates that the charging current is well regulated and therefore known when the interface load is in place. Serious overcharging or undercharging of the batter is thus prevented in the event of an unknown implant depth within the limits shown plotted. This simple arrangement obviates the need for more complex and less reliable electronic regulation, but additional electronic regulation may be employed at a much reduced stress in conjunction with the shorted turn regulator.

A suitable electronic circuit for such regulation is included in FIG. 5. Whereas the metallic case effectively functions as the shorted turn 40 and through the action of eddy current losses loads the tuned transmitting induction coil 9 in the just-described charge current regulating system, additional regulation and rectification is provided by a network of diodes $D_1$–$D_6$ and the silver-mercury cell 2 which load the receiver coil 4 located behind the metallic interface. A frequency $f$ is chosen such that the combination of the metallic interface (acting as an energy absorber) and the loaded receiver coil 4 regulates the current into the battery 2 as the distance $d$ varies. When charging the cell, electromagnetic energy is transmitted from the transmitting coil 9 to the receiver coil 4 resulting in an alternating voltage at the output of the receiver coil. On the negative halfswing of the receiver coil voltage, current is supplied to the cell 2 via diode $D_6$ and also to the diode string $D_3$, $D_4$ and $D_5$. The relative magnitudes of the current supplied to each depends on the cell voltage and the particular diodes chosen. The effect is to prevent overcharging of the cell 2 by shunting the current away from the cell as the cell voltage rises. The cell and diode current are reflected as a load to the transmitting coil 9, which modifies the Q in the same manner as the Q loading by the metallic case. The diode string $D_1$, $D_2$ is employed to provide nonlinear loading on the positive halfswing of the receiver coil voltage to aid in the regulation of the transfer of energy as a function of distance between the two coils. Diode $D_1$ is a Zener diode with a breakdown potential chosen sufficiently high so that at a large distance d the received coil voltage is less than the breakdown voltage. The transmitted energy is unaffected since no current flows into diode $D_1$. As the distance $d$ is reduced, however, the diode string of $D_1$ and $D_2$ begins to conduct on the positive halfswing and thereby improves the control of energy transfer through reflection of additional losses from the receiver coil 4 to the transmitting coil 9. Diode $D_2$ prevents conduction through diode $D_1$ on the negative halfswing.

Figure 9:
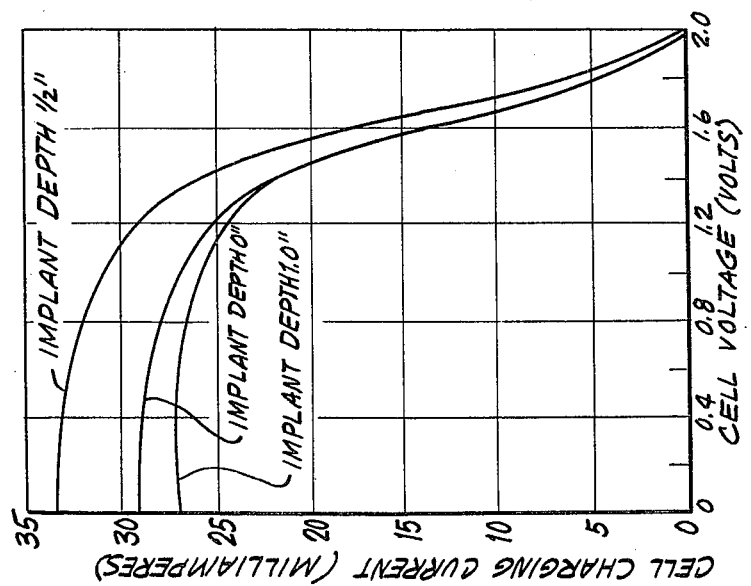
FIG. 9 is a plot of charging current for the pacemaker cell using the techniques of the present invention wherein the curves are drawn for cell voltages from 0 to 2.0 volts and for implant separations of 0, 0.5, and 1.0 inches.
Figure 8:
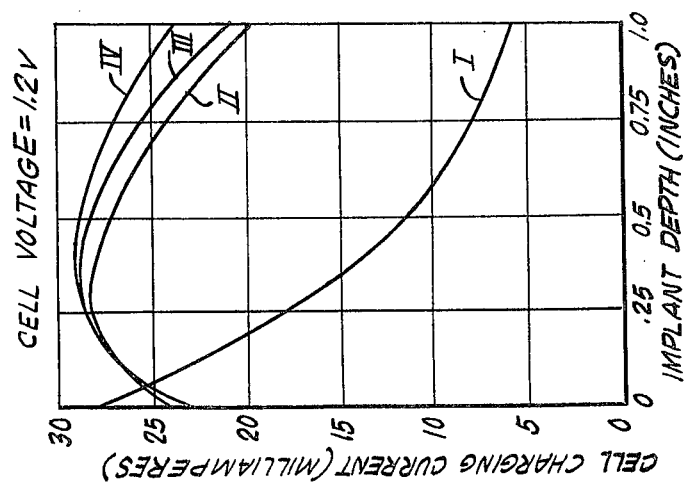
FIG. 8 is a plot illustrating the variation in cell charging current with implant depth at a cell voltage of 1.2 volts using the circuitry of FIG. 5.

The advantageous feature of the overall combination is that the Zener breakdown voltage of diode $D_1$ can be chosen optimally to trim the regulation desired for a particular physical arrangement and for the required charging currents for the cell. A plot is providing in FIG. 8 illustrating the effect on charge current regulation of the various techniques discussed. For each set of data the maximum charge current was adjusted to about 28 milliamps. Curve I shows the charging current for an untuned system. The effect of tuning is shown in curve II in which the effect of the charge current reflected to the transmitting coil provides the regulation. Curve III shows the additional improvement by introduction of a stainless steel interface and curve IV shows the additional improvement employing the Zener diode load. The change in current over a 1.0 inch distance change for the untuned system is 22 milliamps. With the addition of the case and diode loading, the variable is reduced to 4 milliamps over the same variation in implant depth. An important feature of this regulation scheme is the automatic reduction of the transmitted power as the separation distance is reduced. Metallic case heating is thereby much lower for small separation distances than would be encountered in a system employing constant transmit power. FIG. 9 is a plot of charging current for the pacemaker cell using the techniques of the present invention. The curves are drawn for cell voltages from 0 to 2.0 volts and for implant separations of 0, 0.5, and 1.0 inches.

The implant depth may be detected by the meter 17 (FIG. 1) which incorporates built-in rectifier that senses the voltage change on transmitting coil 9 as a result of the change in Q.

It will thus be seen that the present invention provides a safe relatively inexpensive pacemaker, which embodies an outer case, preferably of metal, hermetically sealed against moisture intrusion, and an inner container sealed against cell outgassing that might damage the electronics. A single rechargeable cell may be used to achieve extended long life, in which event the metallic case may be made to act along with the internal electronics as a charging current regulator system maintaining a substantially constant power transfer from the transmitter to the receiver despite variations in their proximate spacing.

We claim:
1. A cardiac pacer system comprising:
an integral metallic casing having an opening therein;
cover means for closing said opening having its periphery recessed within and abutting the interior of said opening to form an external receptacle in said casing;
sealing means closing the seam formed by the abutment of the periphery of said cover means and the interior of said opening for hermetically sealing said cover means to said casing;
biocompatible means disposed in said receptacle for isolating said sealed seam from the exterior of said casing;
means in said casing for producing pacing pulses;
lead means connected to said pulse producing means and passing through said cover means for conducting said pacing pulses out of said casing;
rechargeable power cell means in said casing for powering said pulse producing means; and
means for recharging said power cell means comprising:
a first inductance in said casing disposed adjacent a metallic wall of said casing for receiving electromagnetic energy through said wall; and
tuned circuit means disposed outside of said casing for transmitting electromagnetic energy through said metallic wall to said first inductance, said tuned circuit means comprising a second inductance and a capacitance tuned such that said metallic wall acts as a shorted turn to absorb energy between said first inductance and said circuit means and modify the transmitted energy as a function of the distance between said wall and said second inductance.
2. A system as in claim 1 further comprising container means in said casing for housing said rechargeable cell means;
getter means in said container means for absorbing gas given off by said cell means; and
means for hermetically sealing said container means.
3. A system as in claim 2 wherein said getter means is of a material selected from the group consisting of palladium sponge and lanthanum pentanickel.
4. A system as in claim 1 further comprising:
electrode means connected to said lead means for conducting said pacing pulses to the heart of a patient;
means for connecting said electrode means and said lead means; and
feedthrough means in said cover means for passing said lead means out of said casing;
and wherein said connecting means and said feedthrough means are disposed within said biocompatible means.
5. A system as in claim 4 wherein said biocompatible means comprises a biocompatible epoxy.
6. A system as in claim 1 wherein said recharging means further comprises a first diode connected in series with said first inductance and said power cell means;
second, third and fourth diodes connected in series with each other with like polarity and in parallel with said first inductance; and
a fifth diode and a Zener diode connected with opposite polarity in series with each other and in parallel with said first diode and said power cell means, the polarity of said Zener diode being the same as that of said second, third and fourth diodes.
7. A system as in claim 1 wherein said metallic casing is of stainless steel and said sealing means comprises low temperature silver solder.
8. A system as in claim 1 wherein said cover means comprises a plate member having an upstanding peripheral lip and said sealing means comprises a weld disposed around the uppermost edge of said lip to close the seam between said lip and said interior of said opening.
9. A system as in claim 1 wherein said rechargeable power cell means comprises a silver modified zinc-mercury battery.
10. A rechargeable cardiac pacer system comprising:
an implantable pacer unit having a metallic casing;
electronic means in said casing for producing pacing pulses;
means for conducting said pacing pulses out of said casing;
rechargeable power cell means in said casing for powering said electronic means;
means for recharging said cell means in response to externally-induced electrical energy, said recharging means comprising:
a first inductance disposed adjacent a metallic wall of said casing; and
tuned circuit means disposed outside of said casing adjacent said metallic wall for transmitting electrical energy through said metallic wall into said first inductance, said tuned circuit comprising a second inductance and a capacitance tuned such that said metallic wall acts as a shorted turn energy absorber between said first inductance and said circuit means to modify the energy transmitted as a function of the distance between said wall and said second inductance.
11. A system as in claim 10 wherein said recharging means further comprises a first diode connected in series with said first inductance and said power cell means;

second, third and fourth diodes connected in series with each other with like polarity and in parallel with said first inductance; and a fifth diode and a Zener diode connected with opposite polarity in series with each other and in parallel with said first inductance and said power cell means, the polarity of said Zener diode being the same as that of said second, third and fourth 12. A system as in claim 10 wherein said rechargeable power cell means comprises a silver modified zinc-mercury battery.

13. A cardiac pacer comprising:
an outer casing;
electronic means for producing pacing pulses contained in said casing;
rechargeable power cell means in said casing for powering said electronic means;
means for conducting said pacing pulses out of said casing
getter means in said container means for absorbing gas given off by said cell; and
means for recharging said power cell means comprising:
an induction coil in said casing;
a first diode connected in series with said induction coil and said power cell means;
second, third and fourth diodes connected in series with each other with like polarity and in parallel with said first diode and said power cell means; and
a fifth diode and a Zener diode connected with opposite polarity in series with each other and in parallel with said induction coil, the polarity of said Zener diode being the same as that of said second, third and fourth diodes.

14. A pacer as in claim 13 further comprising:
container means in said casing for housing said power cell means;
getter means in said container means for absorbing a gas given off by said cell means; and
means for hermetically sealing said container means.

15. A pacer as in claim 13 wherein zinc-mercury battery. rechargeable power cell means comprises a silver modified zinc-mercurybattery.

16. An hermetically sealed cardiac pacer comprising:
an integral metallic casing having an opening therein;
cover means for closing said opening having its periphery recessed within and juxtaposed to the interior periphery of said opening to form an external receptacle in said casing;
sealing means closing the seam formed by the juxtaposed peripheries of said cover means and the interior of said opening for hermetically sealing said cover means to said casing;
biocompatible means disposed in said receptacle for isolating said seal seam from the exterior of said housing
means in said casing for producing pacing pulses;
means passing through said cover means for conducting said pacing pulses out of said casing;
rechargeable power cell means in said casing for powering said pulse producing means; and
means for recharging said power cell means comprising:
an induction coil in said casing disposed immediately adjacent a metallic wall of said casing;
a first diode connected in series with said induction coil and said power cell means;
second, third and fourth diodes connected in series with each other with like polarity and in parallel with said first diode and said power cell means; and a fifth diode and a Zener diode connected with opposite polarity in series with each other and in parallel with said induction coil, the polarity of said Zener diode being the same as that of said second, third and fourth diodes.

17. A pacer as in claim 16 wherein said casing comprises a box-like enclosure having congruent front and rear faces and two similar edge members bridging said faces and cooperating therewith to form a substantially four-sided end opening and said cover means comprises a plate member disposed within said opening with its periphery adjacent the interior walls of said end opening a predetermined distance from the outer edge of said opening so as to close the interior of said casing and form said external receptacle therein.

18. A pacer as in claim 16 wherein said casing comprises a cylindrical enclosure having said opening at one end and said cover means comprises a circular cap member disposed within said opening with its periphery adjacent the interior walls of said end opening a predetermined distance from the outer edge of said opening so as to close the interior of said casing and form said external receptacle therein.

19. A pacer as in claim 16 wherein said metallic casing is of stainless steel and said sealing means comprises low temperature silver solder.

20. A pacer as in claim 16 further comprising biocompatible means disposed in said receptacle for isolating said sealed seam from the exterior of said casing.

21. A pacer as in claim 16 wherein said cover means comprises a plate member having an upstanding peripheral lip and said sealing means comprises a weld disposed around the uppermost edge of said lip to close the seam between said lip and said interior of said opening.

22. A pacer as in claim 15 further comprising:
container means in said casing for housing said power cell means;
getter means in said container means for absorbing gas given off by said cell means; and
means for hermetically sealing said container means.

23. A pacer as in claim 16 wherein said rechargeable power cell means comprises a silver modified zinc-mercury battery.

24. A pacer as in claim 23 further comprising:
container means in said casing for housing said power cell means; and
getter means in said container means for absorbing gas given off by said power cell means.

25. A recharging system for implantable cardiac pacers or the like comprising:
an implantable pacer housing having a metallic wall;
means disposed within said housing adjacent said metallic wall for picking up electrical energy induced therein from outside of said housing;
rechargeable power cell means inside said housing and operatively connected to said pick-up means for receiving the electrical energy induced therein; and
means for inducing electrical energy into said pick-up means through said metallic wall from outside of said housing, said inducing means comprising:

tuned circuit means, disposed outside said housing for transmitting electrical energy through said metallic wall to said pick-up means, and comprising an inductance and a capacitance tuned such that said metallic wall acts as a shorted turn energy absorber between said pick-up means and said inducing means to modify the transmission level of said electrical energy as a function of the distance between said inductance and said wall.

26. A system as in claim 25 wherein said pick-up means comprises a second inductance and said rechargeable power cell means further comprises:
a rechargeable power cell;
a first diode connected in series with said second inductance and said power cell;
second, third and fourth diodes connected in series with each other with like polarity and in parallel with said second inductance; and
a fifth diode and a Zener diode connected with opposite polarity in series with each other and in parallel with said second inductance, the polarity of said Zener diode being the same as that of said second, third and fourth diodes.

27. A system as in claim 25 wherein said rechargeable power cell means comprises a silver modified zinc-mercury battery.

* * * * *

UNITED STATES PATENT AND TRADEMARK OFFICE
CERTIFICATE OF CORRECTION

PATENT NO. : 4,014,346

DATED : March 29, 1977

INVENTOR(S) : ROBERT R. BROWNLEE; G. FRANK O. TYERS and CARL VOLZ, SR.

It is certified that error appears in the above-identified patent and that said Letters Patent are hereby corrected as shown below:

Col. 2, line 44, "signals" should read --signal--;

Col. 4, line 54, "follows" should read --followed--;

Col. 6, line 3, "batter" should read --battery--;
 line 55, "providing" should read --provided--;

Claim 11, last line, "fourth" should read --fourth diodes.--;

Claim 13, lines 9, 10, "getter means in said container means for absorbing gas given off by said cell" should be deleted;

Claim 15 should read --15. A pacer as in claim 13 wherein said rechargeable power cell means comprises a silver modified zinc-mercury battery.--

Claim 16, lines 11-13 should be deleted in their entirety;

Claim 22, line 1, the dependency should read --16--.

Signed and Sealed this

Thirty-first Day of May 1977

[SEAL]

Attest:

RUTH C. MASON
*Attesting Officer*

C. MARSHALL DANN
*Commissioner of Patents and Trademarks*